US012521535B2

(12) United States Patent
Keaton

(10) Patent No.: US 12,521,535 B2
(45) Date of Patent: Jan. 13, 2026

(54) DILATION SYSTEM AND METHOD OF USING THE SAME

(71) Applicant: E. P. Keaton, Winston Salem, NC (US)

(72) Inventor: E. P. Keaton, Winston Salem, NC (US)

( * ) Notice: Subject to any disclaimer, the term of this patent is extended or adjusted under 35 U.S.C. 154(b) by 229 days.

(21) Appl. No.: 18/233,145

(22) Filed: Aug. 11, 2023

(65) Prior Publication Data

US 2025/0050077 A1 Feb. 13, 2025

(51) Int. Cl.
*A61M 29/00* (2006.01)

(52) U.S. Cl.
CPC ..... *A61M 29/00* (2013.01); *A61M 2210/1067* (2013.01)

(58) Field of Classification Search
CPC . A61M 29/00; A61M 2210/1067; A61B 1/31; A61B 5/0093; A61H 19/44; A61H 19/50; A61H 19/40; A61H 21/00
See application file for complete search history.

(56) References Cited

U.S. PATENT DOCUMENTS

| | | | | |
|---|---|---|---|---|
| 1,879,305 | A | 9/1932 | Kennedy | |
| 2,290,571 | A * | 7/1942 | Peyton | A61M 29/00 604/104 |
| 3,675,642 | A * | 7/1972 | Lord | A61M 29/00 600/32 |
| 3,916,906 | A | 11/1975 | Gerry | |
| 4,263,914 | A * | 4/1981 | Pawlak | A61H 21/00 601/112 |
| 4,563,182 | A * | 1/1986 | Stoy | A61F 5/0093 607/113 |
| 4,938,221 | A | 7/1990 | Tuffel | |
| 6,623,503 | B1 * | 9/2003 | Thomas | A61M 29/00 606/191 |
| 9,511,209 | B2 | 12/2016 | Draster et al. | |
| 2012/0296272 | A1 | 11/2012 | Bidault et al. | |
| 2023/0165701 | A1 | 6/2023 | Gobel | |

* cited by examiner

*Primary Examiner* — Sarah A Long
(74) *Attorney, Agent, or Firm* — Ashley D. Johnson; Dogwood Patent and Trademark Law

(57) ABSTRACT

The invention is an anal dilation system that can be used to effectively dilate the rectal sphincter muscles of a user. The system includes a combination of anal plugs and anal wands, each with graduated and coordinated girths that cooperate to achieve a desired dilation of the sphincter muscle. The system can be used to achieve dilation of the sphincter muscle easily, quickly, and with less discomfort compared to current systems.

19 Claims, 6 Drawing Sheets

DILATION SYSTEM AND METHOD OF USING THE SAME

TECHNICAL FIELD

The presently disclosed subject matter is directed to a dilation system comprising a plurality of plugs and wands of varying diameters. The presently disclosed subject matter further comprises methods of using the disclosed system to dilate the sphincter muscles of a user.

BACKGROUND

Traditional rectal dilators for anal dilation are generally configured as a series of plugs with different diameters that accomplish rectal expansion by the successive insertion of larger diameter dilators. The significant increase in size from one plug to the next can make it difficult and uncomfortable to transition to the next larger size. In addition, the general shape of traditional anal plugs requires the sphincter muscle of a user to stretch to accommodate the largest section of the bulb very briefly as it passes through. The sphincter then relaxes to the much smaller girth of the neck of the plug. The smaller girth is necessary for the wearer to be able to leave the plug in hands-free, but it is inefficient at achieving comfortable dilation to the desired girth. It would therefore be beneficial to provide an improved anal dilation system that allows users to achieve rectal expansion easily and more comfortably compared to current systems.

SUMMARY

The presently disclosed subject matter comprises a dilation system that includes a plurality of plugs. Each plug includes a base with a top face and an opposed bottom face, and a thickness therebetween; a neck with a top face and a bottom face and a thickness therebetween, wherein the top face of the base is in direct contact with the bottom face of the neck; and a bulb comprising a bottom face that tapers into a top tip and a thickness therebetween, wherein the bulb bottom face is in direct contact with the top face of the neck. Each bulb comprises a maximum bulb diameter. The system further comprises a plurality of wands, each wand comprising a base with a top face and an opposed bottom face and thickness therebetween; a lower region with a top face, a bottom face, and a thickness therebetween, wherein the top face of the wand base is in direct contact with the bottom face of the lower region and wherein the lower region has a maximum diameter; a neck with a top face and a bottom face and a thickness therebetween, wherein the top face of the lower region is in direct contact with the bottom face of the neck; a knot with a top face, a bottom face, and a thickness therebetween, wherein the bottom face of the knot is in direct contact with the top face of the neck, and wherein the knot has a maximum diameter; and a nose comprising a bottom face and a tapered top with a thickness therebetween, wherein the nose bottom face is in direct contact with the top face of the knot.

In some embodiments, the system includes a first wand, a first plug, a second wand, and a second plug. The maximum diameter of the lower region of a first wand is the same as the bulb maximum diameter of a first plug. The maximum diameter of the bulb of the first plug and the maximum diameter of the lower region of the first wand are the same as the maximum diameter of the knot of a second wand. The maximum diameter of the lower region of the second wand is greater than the maximum diameter of the second wand knot. The maximum diameter of the lower region of the second wand is the same as the maximum diameter of the bulb of a second plug.

In some embodiments, each bulb maximum diameter is about 1-3 inches.

In some embodiments, each bulb thickness is about 1.5-4 inches.

In some embodiments, each wand lower region thickness, each knot thickness, or both are about 1-4 inches.

In some embodiments, the maximum diameter of each wand lower region is 1-3 inches.

In some embodiments, the maximum diameter of each wand neck, plug neck, or both is 0.5-2 inches.

In some embodiments, the maximum diameter of each knot is about 0.5-2.5 inches.

In some embodiments, each wand and plug is constructed from rubber, silicone, plastic, metal, glass, or combinations thereof.

In some embodiments, the system comprises three or more plugs and three or more wands.

In some embodiments, the presently disclosed subject matter is directed to a method of dilating the rectum of a user. Specifically, the method comprises inserting a first wand of the disclosed system into the rectum, such that the base is external to the body but the knot and the lower region are within the rectum. Once the rectum has stretched, the first wand is removed and replaced in the rectum with a first plug. The maximum diameter of the first plug bulb is the same as the maximum diameter of the first wand lower region.

In some embodiments, the method includes removing the first plug and inserting a second wand, the second wand comprising a knot maximum diameter that is the same as the first plug bulb maximum diameter, and the second wand lower region maximum diameter is the greater than the maximum diameter of the second wand knot. Once the rectum has stretched, removing the second wand and replacing the second wand in the rectum with a second plug. The maximum diameter of the second plug bulb is the same as the maximum diameter of the second wand lower region.

BRIEF DESCRIPTION OF THE DRAWINGS

The previous summary and the following detailed descriptions are to be read in view of the drawings, which illustrate some (but not all) embodiments of the presently disclosed subject matter.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms “a”, “an”, and “the” refer to “one or more” when used in the subject specification, including the claims. Thus, for example, reference to “a device” can include a plurality of such devices, and so forth.

Unless otherwise indicated, all numbers expressing quantities of components, conditions, and so forth used in the specification and claims are to be understood as being modified in all instances by the term “about”. Accordingly, unless indicated to the contrary, the numerical parameters set forth in the instant specification and attached claims are approximations that can vary depending upon the desired properties sought to be obtained by the presently disclosed subject matter.

As used herein, the term “about”, when referring to a value or to an amount of mass, weight, time, volume, concentration, and/or percentage can encompass variations of, in some embodiments +/−0.1-20% from the specified amount, as such variations are appropriate in the disclosed packages and methods.

Figure 1:
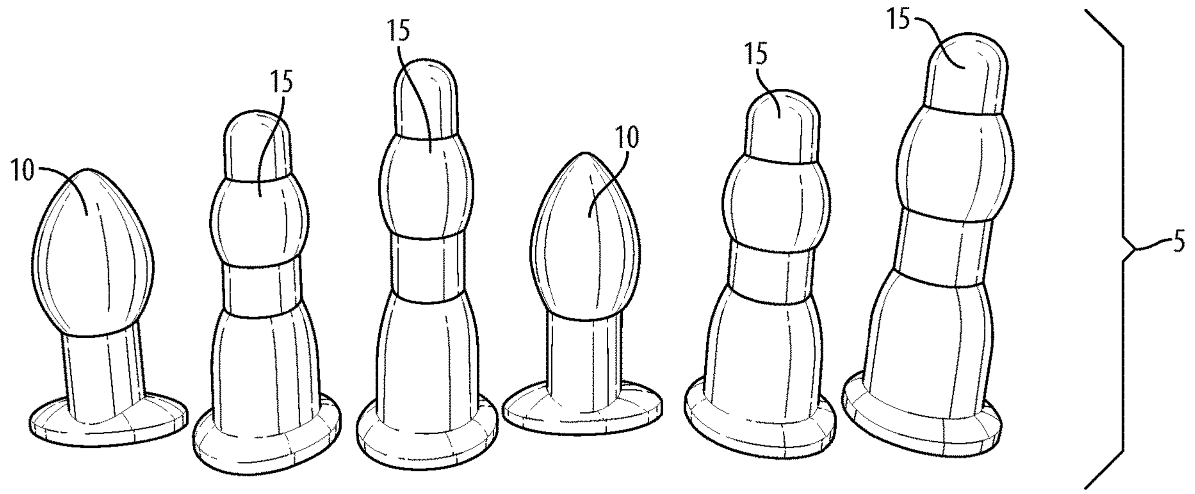
FIG. 1 is a front perspective view of a dilation system in accordance with some embodiments of the presently disclosed subject matter.

The presently disclosed subject matter is directed to an anal dilation system that can be used to effectively dilate the rectal sphincter muscles of a user. As illustrated in FIG. 1, the disclosed system 5 includes a combination of anal plugs 10 and anal wands 15, each with graduated and coordinated girths that cooperate to achieve a desired dilation of the sphincter muscle. As described in detail below, the disclosed system can be used to achieve dilation of the sphincter muscle easily, quickly, and with less discomfort compared to current systems.

Figure 2A:
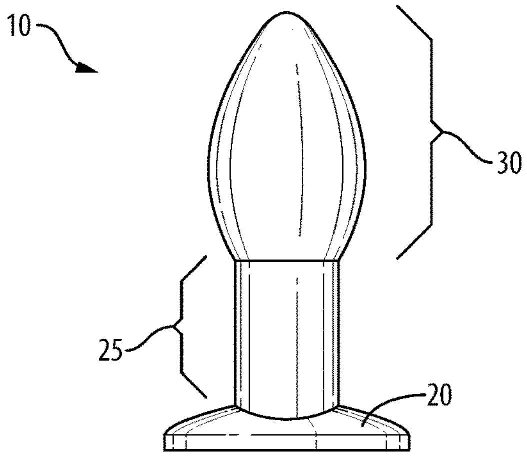
FIG. 2*a* is a front plan view of a dilation system plug in accordance with some embodiments of the presently disclosed subject matter.

As noted above, system 5 includes a plurality of anal plugs 10, each plug comprising a unique girth or diameter compared to the other plugs. The term “plug” as used herein refers to a device configured to be inserted at least partially into the rectum of a user for a desired amount of time. FIG. 2*a* illustrates one embodiment of plug 10 comprising base 20, neck 25, and tapered bulb 30. In use, the base ensures that the plug does not slide into the rectum completely and provides a grip for removing the plug. The neck is enclosed by the sphincter and the bulb contacts the anus.

Figure 2B:
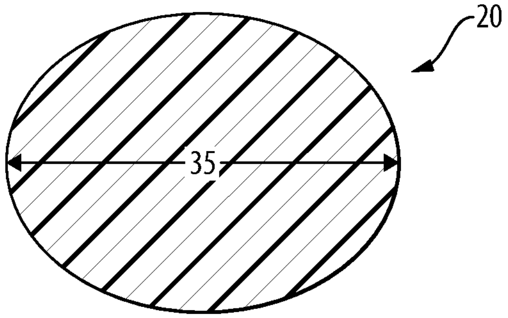
FIG. 2*b* is a cross-sectional view of a plug base in accordance with some embodiments of the presently disclosed subject matter.

The plug base is positioned opposed to tapered bulb 30, and in some embodiments can be configured as a disc. As shown in FIG. 2*b*, the plug base includes diameter 35 that is too large to be inserted into the rectum (e.g., diameter 35 is larger than the anus). In this way, the base can be used to grasp the plug to remove it from the rectum, since it remains external to the body. In some embodiments, the base can have a diameter of about 1.5-3.5 inches or more (e.g., at least/no more than about 1.5, 2, 2.5, 3, 3.5, 4, 4.5, 5, 5.5, 6, 6.5, 7, 7.5, 8, 8.5, 9, 9.5, or 10 inches). However, the presently disclosed subject matter is not limited and the base can have any suitable diameter. The term “diameter” refers to the length of the longest straight line passing from side to side through the center of a body, element, or feature, and does not impart any structural configuration on the body, element, or feature. It should be appreciated that the diameter of the base makes up the largest diameter of the entire plug (e.g., the diameter of the plug bulb is less than the diameter of the plug base).

Figure 2C:
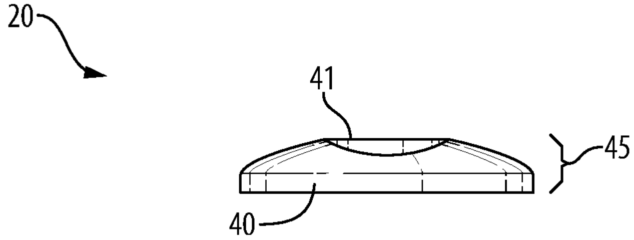
FIG. 2*c* is a front plan view of a plug base in accordance with some embodiments of the presently disclosed subject matter.

As shown in FIG. 2*c*, the base includes bottom face 40 and opposed top face 41 with thickness 45 therebetween. The bottom face of the base can be horizontal in some embodiments, allowing the plug to rest on a supporting surface during storage (e.g., a table). However, the bottom face and top faces are not limited and can have any orientation.

Base 20 can have any suitable thickness 45 (e.g., the vertical distance between top and bottom faces 40, 41). For example, the base can have a thickness of at least/no more than about 0.1-0.5 inches (e.g., at least/no more than about 0.1, 0.2, 0.30, 0.4, or 0.5 inches). However, it should be appreciated that the base can have any desired thickness and is not limited to the range given above.

Base 20 can have any desired cross-sectional shape, such as the oval shape shown in FIG. 2*b*. However, the shape of the base is not limited and can be configured in any desired shape so long as it can be grasped by a user (e.g., circular, square, rectangular, pentagonal, heart-shaped, and the like).

Figure 2D:
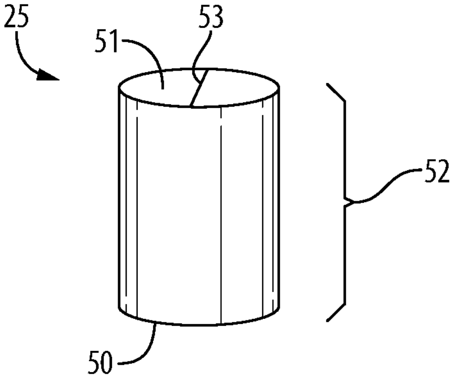
FIG. 2*d* is a perspective view of a plug neck in accordance with some embodiments of the presently disclosed subject matter.
Figure 2E:
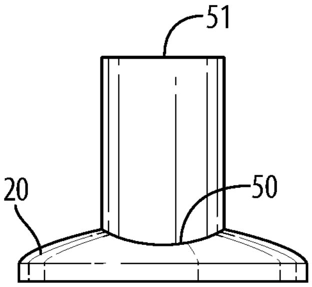
FIG. 2*e* is a front plan view of a plug base and neck in accordance with some embodiments of the presently disclosed subject matter.

As set forth above, the plug also includes neck 25, as illustrated in FIG. 2*d*. The neck includes bottom face 50 and opposed top face 51 with thickness 52 therebetween. Bottom face 50 of the neck is directly adjacent to top face 41 of the base, as shown in FIG. 2*e*.

The neck can include any suitable thickness, such as at least/no more than about 0.25-3 inches (e.g., 0.25, 0.5, 0.75, 1, 1.25, 1.5, 1.75, 2, 2.25, 2.5, 2.75, or 3 inches). However, the thickness dimensions are not limited and can be greater or less than the given range.

The neck can further include diameter 53 of about 0.5-2 inches (e.g., at least/no more than about 0.5, 0.75, 1, 1.25, 1.5, 1.75, or 2 inches). The diameter of the neck will always be less than the diameter of the bulb. For example, the diameter of the neck can be about 10-50 percent less than the diameter of the bulb. It should be appreciated that the diameter of neck 25 can be configured outside the given range and is not limited.

In some embodiments, the neck can have a round or oval cross-sectional shape for comfort when inserted into the rectum (e.g., no sharp edges).

Figure 2F:
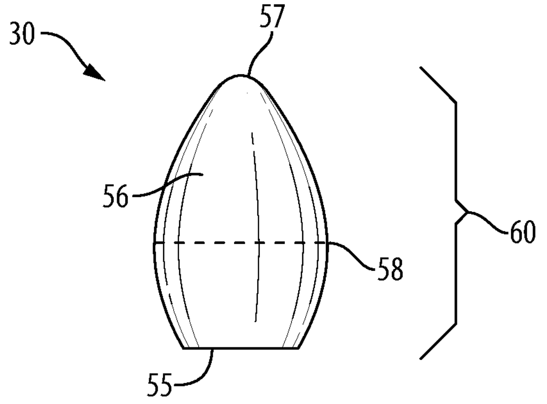
FIG. 2*f* is a front plan view of a plug bulb in accordance with some embodiments of the presently disclosed subject matter.
Figure 2G:
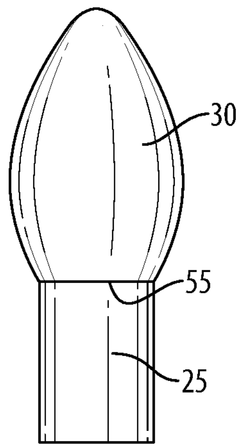
FIG. 2*g* is a front plan view of a plug bulb and neck in accordance with some embodiments of the presently disclosed subject matter.

One embodiment of plug bulb 30 is illustrated in FIG. 2*f*. As shown, the bulb includes lower face 55 and rounded body 56 that ends in tapered end 57. The lower bulb face is directly in contact with the upper face of neck 25, as shown in FIG. 2*g*.

At the widest point (indicated as element 58), the bulb can include a diameter of about 1-3 inches (e.g., at least/no more than about 1, 1.5, 2, 2.5, or 3 inches). The diameter of the bulb is selected to ensure that the plug remains within the rectum and cannot be inadvertently removed until desired by the user. The diameter of the bulb is further selected to provide a desired amount of stretching of the sphincter muscle, as described below. The diameter of the bulb is not limited and can be configured outside the given range (e.g., 10, 20, 30, 40, or 50 percent more or less than the range).

The bulb can further include height 60 (e.g., the vertical distance from bottom face 55 to tapered end 57) of about 1.5-4 inches (e.g., at least/no more than about 1.5, 2, 2.5, 3, 3.5, or 4 inches). It should be appreciated that the height is not limited to the given range.

Figure 3A:
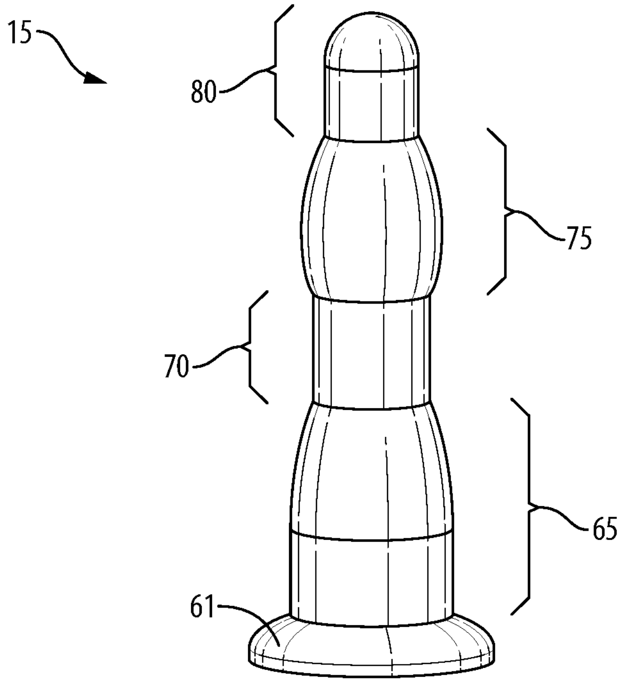
FIG. 3*a* is a front plan view of a system wand in accordance with some embodiments of the presently disclosed subject matter.

The disclosed system also includes a plurality of anal wands 15. The term “wand” refers to a phallic shaped device that is designed to be inserted into the rectum. The diameter of each wand increases gradually from top to bottom to achieve dilation of the sphincter muscle. As illustrated in FIG. 3*a*, each wand includes base 61, widened lower region 65, tapered neck 70, knot 75 and nose 80.

Figure 3B:
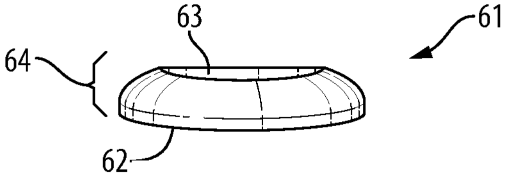
FIG. 3*b* is a front plan view of a wand base in accordance with some embodiments of the presently disclosed subject matter.

As shown in FIG. 3*b*, wand base 61 includes bottom face 62 and opposed top face 63 with thickness 64 therebetween. The bottom face of the wand can be horizontal in some embodiments, allowing the wand to rest on a supporting surface during storage (e.g., a table). However, the bottom face is not limited and can have any configuration.

As with the plug, the wand base includes a diameter that is too large to be inserted into the rectum (e.g., the wand base diameter is larger than the opening of the rectum). In this way, the base can be used to grasp the wand to remove it from the rectum, since it remains external to the body. In some embodiments, base 61 can have a diameter of about 1.5-3.5 inches or more (e.g., at least/no more than about 1.5, 2, 2.5, 3, 3.5, 4, 4.5, 5 inches). However, the presently disclosed subject matter is not limited and the base can have any suitable diameter.

Base 61 can have any suitable thickness 64 (e.g., the vertical distance between top and bottom faces 62 and 63). For example, the wand base can have a thickness of at least/no more than about 0.1-0.5 inches (e.g., at least/no more than about 0.1, 0.2, 0.3, 0.4, or 0.5 inches). However, it should be appreciated that the base can have any desired thickness and is not limited to the range given above.

Base 61 can have any desired cross-sectional shape, such as circular or oval, rectangular, square, triangular, heart-shaped, diamond-shaped, and the like. It should be appreciated that the wand base can be configured in any desired shape so long as it can 10 be grasped by a user.

Figure 3C:
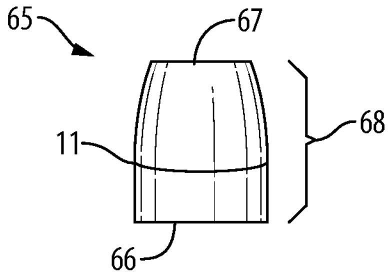
FIG. 3*c* is a front plan view of a wand lower region in accordance with some embodiments of the presently disclosed subject matter.
Figure 3D:
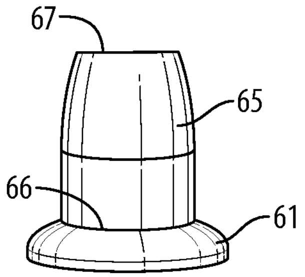
FIG. 3*d* is a front plan view of a wand base and lower region in accordance with some embodiments of the presently disclosed subject matter.

As noted above, the wand further includes lower region 65 that comprises lower face 66 and opposed upper face 67 with thickness 68 therebetween. As shown in FIG. 3*c*, the lower region tapers from the lower face to the upper face. For example, the diameter of the lower face of the lower region can be about 1-3 inches (e.g., at least/no more than about 1, 1.25, 1.5, 1.75, 2, 2.25, 2.5, 2.75, or 3 inches), while the diameter of the upper face can be about 0.5-2 inches (e.g., at least/no more than about 0.5, 0.75, 1, 1.25, 1.5, 1.75, or 2 inches). The lower region thickness 68 can be about 1-4 inches (e.g., at least/no more than about 1, 1.5, 2, 2.5, 3, 3.5, or 4 inches). As shown in FIG. 3*d*, lower face 66 directly contacts upper face 63 of the wand base.

Importantly, the diameter of the lower region of a particular wand (illustrated as element 11 in FIG. 3*c*) is the same or about the same as the largest diameter of a corresponding bulb of a plug, as described in detail below. Thus, the lower region of the wand can dilate the sphincter muscle of a user to a desired level. The dilation can be maintained by a corresponding plug 10 with a bulb of the same diameter as the diameter of the lower region of the wand. The diameter of the knot of the wand is less than the diameter of the lower region, functioning to ease insertion of the wand during use. This allows for a larger diameter of wand to be used more quickly and easily.

Figure 3E:
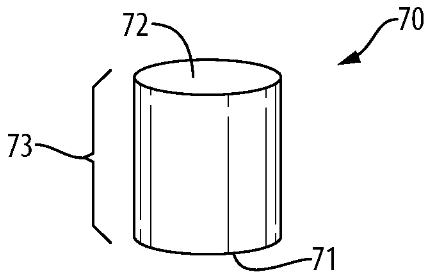
FIG. 3*e* is a perspective view of a wand neck in accordance with some embodiments of the presently disclosed subject matter.

As set forth above, the wand also includes neck 70, as illustrated in FIG. 3*e*. The neck includes bottom face 71 and opposed top face 72 with thickness 73 therebetween. The neck can include any suitable thickness, such as at least/no more than about 0.5-3 inches or more (e.g., 0.5, 1, 1.5, 2, 2.5, or 3 inches). The neck can further include a diameter of about 0.5-2 inches (e.g., at least/no more than about 0.5, 0.75, 1, 1.25, 1.5, 1.75, or 2 inches). As described in detail below, the neck can dilate the sphincter muscle when inserted into the rectum. It should be appreciated that the neck diameter can have a diameter and thickness outside the given ranges.

In some embodiments, the neck can have a round or oval cross-sectional shape for comfort when inserted into the rectum (e.g., no sharp edges).

Figure 3F:
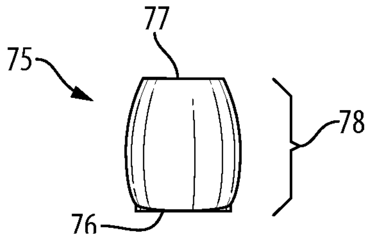
FIG. 3*f* is a front plan view of a wand knot in accordance with some embodiments of the presently disclosed subject matter.

Wand 15 further includes knot 75 as illustrated in FIG. 3*f*. The knot includes lower face 76, opposed upper face 77 and thickness 78 therebetween. As shown in FIG. 3*f*, the knot has a bulbous shape and tapers from the lower face to the upper face. For example, the diameter of the lower face of the knot can be about 0.5-2 inches (e.g., at least/no more than about 0.5, 0.75, 1, 1.25, 1.5, 1.75, or 2 inches), while the diameter of the upper face can be about 0.5-1.5 inches (e.g., at least/no more than about 0.5, 0.75, 1, 1.25, or 1.5 inches). The knot thickness 78 can be about 1-4 inches (e.g., at least/no more than about 1, 1.5, 2, 2.5, 3, 3.5, or 4 inches).

It should be appreciated that the greatest diameter of a particular knot on a wand is less than the greatest diameter of the lower region. (e.g., at least/no more than about 1, 5, 10, 15, 20, or 25 percent less).

Figure 3G:
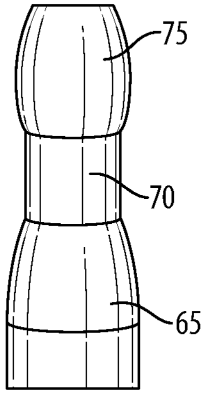
FIG. 3*g* is a front plan view of a wand knot, neck, and lower region in accordance with some embodiments of the presently disclosed subject matter.

As shown in FIG. 3*g*, neck 70 is positioned between the knot and the lower region of the wand. Specifically, neck upper face 72 is in direct contact with lower face 76 of the knot. In addition, neck lower face 71 is in direct contact with the upper face of lower region 65.

Figure 3H:
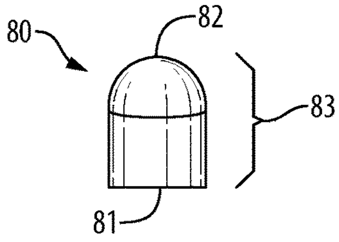
FIG. 3*h* is a front plan view of a wand nose in accordance with some embodiments of the presently disclosed subject matter.
Figure 3I:
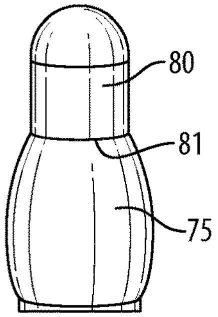
FIG. 3*i* is a front plan view of a wand nose and knot in accordance with some embodiments of the presently disclosed subject matter.

The wand further includes tapered nose 80 that forms the uppermost portion of the wand. As shown in FIGS. 3*h* and 3*i*, the nose includes lower face 81 that is in direct contact with upper face 77 of the knot. The nose also includes tip 82 and thickness 83. In some embodiments, the thickness of the nose (e.g., the distance between tip 82 and nose lower face 81) can be about 0.5-2 inches. Thus, the thickness of the nose can be about 0.5, 1, 1.5, or 2 inches).

Plug 10 and wand 15 can be constructed from any suitable material, such as (but not limited to) rubber, silicone, plastic, glass, metal (e.g., stainless steel), and the like. Further, the material selected for the plugs and wand should be sufficiently rigid to allow the device to be introduced into the rectum. The materials selected should be biocompatible and suitable for contact with human tissue.

Figure 4:
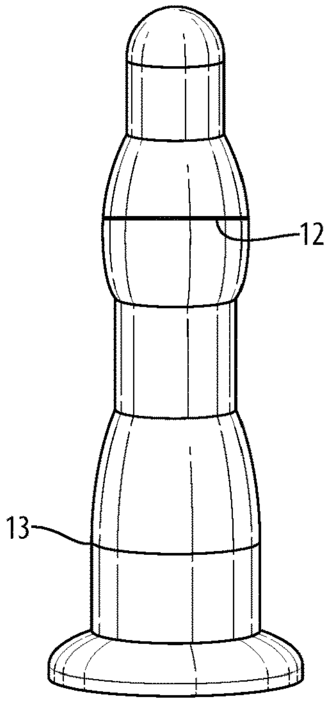
FIG. 4 is a front plan view of a wand with maximum knot and lower region diameters indicated in accordance with some embodiments of the presently disclosed subject matter.

In use, a first wand (e.g., wand with the smallest circumference) is introduced by the user through the anal canal and into the rectum. Due to the shape of the wand, the tapered top end allows knot 75 to ease the transition to the lower region 65 (which has a comparatively larger diameter). Specifically, because the maximum diameter of the knot (illustrated as element 12 in FIG. 4) is less than the maximum diameter of the wand lower region 65 (illustrated as element 13), the insertion of the wand is less painful as the anus is slowly stretched to accommodate the wand regions. The anal muscle then grasps and holds the wand in position until it is removed. When the first wand can be inserted without undue sphincter resistance, the user can proceed with the second wand (larger in diameter than the first wand). Similarly, when the second wand can be comfortably inserted without undue sphincter resistance, the user can proceed with the third wand (larger in diameter than the second wand), and so forth.

Figure 5:
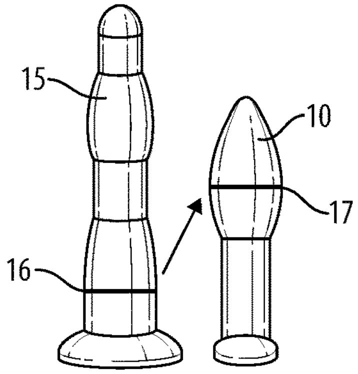
FIG. 5 is a front plan view of a first wand and plug illustrating the maximum plug bulb diameter and maximum wand lower region diameter in accordance with some embodiments of the presently disclosed subject matter.

Wands 15 are not left in the body for prolonged periods of time (e.g., while walking around or doing other tasks). They are primarily used to stretch the rectum easily and more comfortably in preparation for plug 10 (which is worn for extended periods of time). Because lower region 65 of a first wand has the same maximum diameter (element 16 in FIG. 5) as the maximum diameter of a first plug bulb 30 (element 17), the plug can be easily inserted once the sphincter is relaxed by using the wand. The user then wears the first plug for a desired amount of time (e.g., while performing daily tasks) until the user feels ready for transiting to a wand/plug combination with a larger diameter.

When the user is ready for the larger size combination, the user can remove the first plug and slowly insert the second wand into the rectum. The knot of the second wand has the same maximum diameter as the maximum diameter of the bulb of the first plug, thereby allowing the user to comfortably insert the wand before moving on to the lower region of the second wand (which has a diameter that is larger than the knot diameter). As with the first plug and wand, the second wand has a lower region with the same maximum diameter as the bulb of the second plug. Relaxing at the lower region of the second wand therefore makes the second plug easier to insert.

Figure 6:
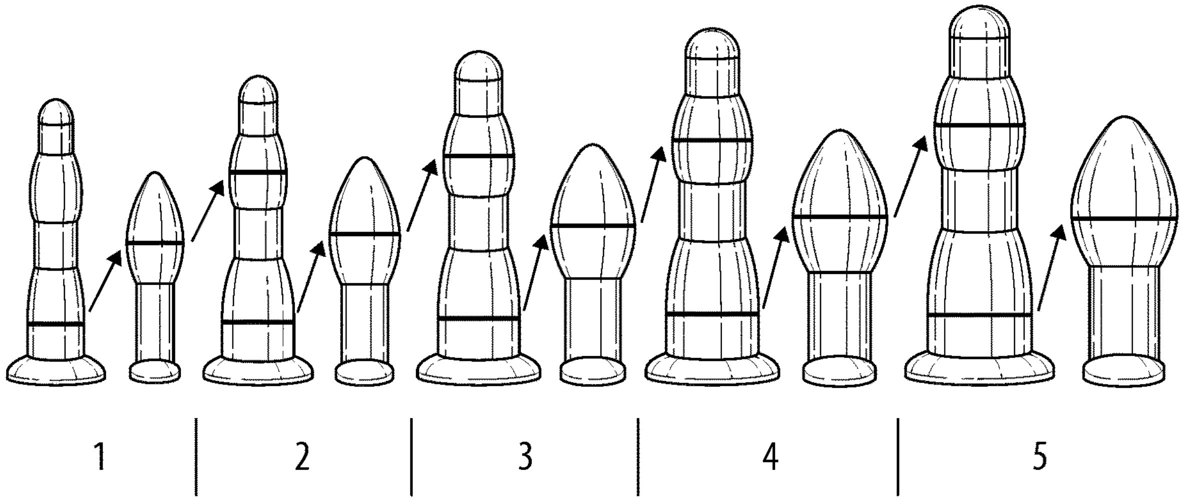
FIG. 6 is a front plan view of a rectal expansion system in accordance with some embodiments of the presently disclosed subject matter.

The process is then repeated for successive wand and plug combinations until the user has reached their desired level of anal stretching, as shown in FIG. 6 and Table 1, below. The black bands in FIG. 6 illustrate a maximum diameter of a particular region of the wand or plug, and the arrows point to/connect regions with the same or about the same diameter. Thus, the maximum diameter of the lower region of the first wand is the same as the maximum diameter of the first plug bulb and the second wand knot.

Table 1 below illustrates representative maximum diameter values for representative wand knot, wand lower region, and plug bulb for a system, in some embodiments. The levels indicate increasing size with larger wands or plugs.

TABLE 1

| | Maximum Diameter (inches) | | |
|---|---|---|---|
| Level | Wand Knot | Wand Lower Region | Plug Bulb |
| 1 | 0.95 | 1.11 | 1.11 |
| 2 | 1.11 | 1.35 | 1.35 |
| 3 | 1.35 | 1.59 | 1.59 |
| 4 | 1.59 | 1.83 | 1.83 |
| 5 | 1.83 | 2.07 | 2.07 |

Table 2 illustrates one embodiment the maximum circumference of a wand knot, wand lower region, and plug bulb of a system., in some embodiments.

TABLE 2

| | Maximum Circumference (inches) | | |
|---|---|---|---|
| Level | Wand Knot | Wand Lower Region | Plug Bulb |
| 1 | 3.0 | 3.5 | 3.5 |
| 2 | 3.5 | 4.25 | 4.25 |
| 3 | 4.25 | 5.0 | 5.0 |
| 4 | 5.0 | 5.75 | 5.75 |
| 5 | 5.75 | 6.5 | 6.5 |

Table 3 illustrates the maximum diameter and circumference ranges of various elements in a particular system, in some embodiments.

TABLE 3

| Element | Maximum Diameter (inches) | Maximum Circumference Range (inches) |
|---|---|---|
| Plug Bulb | 1-3 | 3.5-6.5 |
| Plug Neck | 0.5-2 | 2.25-4.25 |
| Plug Base | 1-3.5 | — |
| Wand Tip | 0.5-1.5 | — |
| Wand Knot | 0.5-2.5 | 3-5.75 |
| Wand Neck | 0.5-2 | 2.5-4.5 |
| Wand Lower Region | 1-3 | 3.5-6.5 |
| Wand Base | 1.5-3.5 | — |

Table 4 illustrates the thickness range of a particular element of some embodiments of the disclosed system.

TABLE 4

| Element | Thickness (inches) |
|---|---|
| Plug Bulb | 1.5-4 |
| Plug Neck | 0.25-3 |
| Plug Base | 0.1-0.5 |
| Wand Tip | 0.5-2 |
| Wand Knot | 1-4 |
| Wand Neck | 0.5-.3 |
| Wand Lower Region | 1-4 |
| Wand Base | 0.1-0.5 |

Figure 7A:
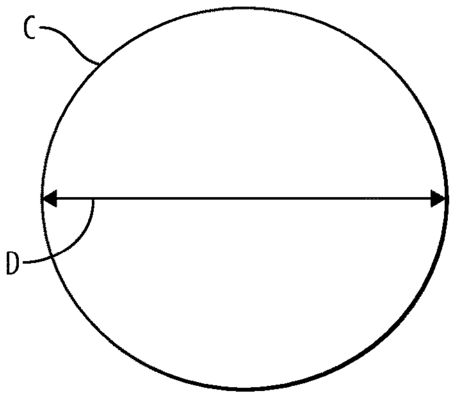
FIGS. 7*a* and 7*b* illustrate the diameter and circumference of an element in accordance with some embodiments of the presently disclosed subject matter.
Figure 7B:
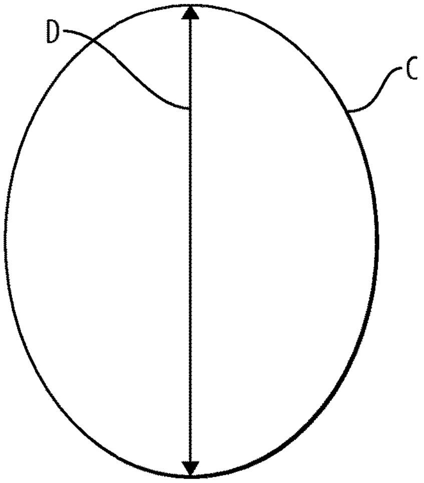

The tables above illustrates that a wand knot of the disclosed system can have a circumference of about 3-6 inches (e.g., at least/no more than about 3, 3.25, 3.5, 4, 4.25, 4.5, 4.75, 5, 5.25, 5.5, 5.75, or 6 inches). The term "circumference" refers to the perimeter, or distance around the exterior surface, of a shape. FIGS. 7*a* and 7*b* illustrate circumference C and diameter D of a shape. The maximum circumference is the largest circumference of a body (e.g., at the widest cross-sectional point). The maximum circumference of a wand lower region can be about 3.5-6.5 inches (e.g., at least/no more than about 3.5, 3.75, 4, 4.25, 4.5, 4.75, 5, 5.25, 5.5, 5.75, 6, 6.25, or 6.5 inches or more). The maximum circumference of a plug bulb can be about 3.5-6.5 inches (e.g., at least/no more than about 3.5, 3.75, 4, 4.25, 4.5, 4.75, 5, 5.25, 5.5, 5.75, 6, 6.25, or 6.5 inches).

As noted above, the bases of the wands and plugs are non-insertable into the rectum of the user. Specifically, the diameters of the bases are larger than the widest insertable portion of the plug or wand to prevent complete insertion and potential harm to the body.

Wands perform most of the stretching of the user's external sphincter muscle. Particularly, the wand is inserted into the rectum such that the knot performs an initial stretch of the same diameter as a current plug, but the lower region of the wand is larger and thereby stretches the sphincter to a larger degree. The next size plug can then be accommodated after the wand has eased the initial stretching. The plug thus holds and maintains dilation until the wearer is ready to move on to the next size.

System 5 offers many advantages over prior art anal dilation systems. For example, the disclosed system combines wands 15 and plugs 10 to achieve comfortable and efficient anal dilation to accommodate a desired girth.

The present invention is safe, simple, and easy to use, and is economical in cost to manufacture, purchase, and distribute.

The system includes a plurality of wands and plugs, each with a unique maximum diameter to stepped insertion progressively to larger diameters.

Removal of the wands and plugs of the disclosed system is not problematic in that the removal procedure is painless and without discomfort.

The system establishes a desired degree of stretching for each size level and then creates a smooth transition between plugs using wands that match and repeat the goal girth. The wand lower regions are responsible for the majority of the anal stretching, so they have been designed as elongated areas of maximum girth to allow the wearer to relax and adjust to the desired size for more efficient dilation when compared to the use of plugs alone.

This system is more comfortable than plug-only systems because the wands create a smooth transition between sizes. It is also more efficient at dilating the sphincter muscle because the elongated bottom of the wand allows the wearer to rest at the thickest section of the wand while the muscles relax as opposed to trying to stretch to the thickest part of a plug, which simply passes through the sphincter during insertion.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A dilation system defined as:

a plurality of plugs, each plug comprising:

a base with a top face, opposed bottom face, and a thickness therebetween;

a neck with a top face, opposed bottom face, and a thickness therebetween, wherein the top face of the base is in direct contact with the bottom face of the neck;

a bulb comprising a bottom face, an opposed tip, and a thickness therebetween, wherein the bulb bottom face is in direct contact with the top face of the neck;

wherein each bulb comprises a maximum bulb diameter;

a plurality of wands, each wand comprising:

a base with a top face, an opposed bottom face, and a thickness therebetween;

a lower region with a top face, an opposed bottom face, and a thickness therebetween, wherein the top face of the wand base is in direct contact with the bottom face of the lower region and wherein the lower region has a maximum diameter;

a neck with a top face, an opposed bottom face, and a thickness therebetween, wherein the top face of the lower region is in direct contact with the bottom face of the wand neck;

a knot with a top face, an opposed bottom face, and a thickness therebetween, wherein the bottom face of the knot is in direct contact with the top face of the wand neck, and wherein the knot has a maximum diameter; and a nose comprising a bottom face, an opposed top, and a thickness therebetween, wherein the nose bottom face is in direct contact with the top face of the knot;

wherein the system comprises a first wand, a first plug, a second wand, and a second plug;

wherein the maximum diameter of the lower region of the first wand is the same as the maximum bulb diameter of the first plug; and wherein the maximum bulb diameter of the first plug and the maximum diameter of the lower region of the first wand are the same as the maximum diameter of the knot of the second wand; and wherein the maximum diameter of the lower region of the second wand is greater than the maximum diameter of the second wand knot; and wherein the maximum diameter of the lower region of the second wand is the same as the maximum bulb diameter of the second plug.

2. The system of claim 1, wherein each plug maximum bulb diameter is about 1-3 inches.

3. The system of claim 1, wherein each plug bulb thickness is about 1.5-4 inches.

4. The system of claim 1, wherein each wand lower region thickness, each knot thickness, or both is about 1-4 inches.

5. The system of claim 1, wherein the maximum diameter of each wand lower region is about 1-3 inches.

6. The system of claim 1, wherein the maximum diameter of each wand neck, plug neck, or both is about 0.5-2 inches.

7. The system of claim 1, wherein the maximum diameter of each knot is about 0.5-2.5 inches.

8. The system of claim 1, wherein each wand and plug is constructed from rubber, silicone, plastic, metal, glass, or combinations thereof.

9. The system of claim 1, comprising three or more plugs and three or more wands.

10. A method of dilating a rectum of a user, the method comprising:

inserting the first wand of the system of claim 1 into the rectum, such that the wand base is external to a body of the user but the knot and the lower region are within the rectum;

once the rectum has stretched, removing the first wand and replacing the first wand in the rectum with the first plug.

11. The method of claim 10, further comprising removing the first plug and inserting the second wand;

wherein once the rectum has stretched, removing the second wand and replacing the second wand in the rectum with the second plug.

12. The method of claim 10, wherein each plug maximum bulb diameter is about 1-3 inches.

13. The method of claim 10, wherein each plug bulb thickness is about 1.5-4 inches.

14. The method of claim 10, wherein the maximum diameter of each wand lower region is about 1-3 inches.

15. The method of claim 10, wherein the maximum diameter of each wand neck, plug neck, or both is about 0.5-2 inches.

16. The method of claim 10, wherein the maximum diameter of each knot is about 0.5-2.5 inches.

17. The method of claim 10, wherein each wand and plug is constructed from rubber, silicone, plastic, metal, glass, or combinations thereof.

18. The method of claim 10, comprising three or more plugs and three or more wands.

19. The method of claim 10, wherein each wand lower region thickness, each knot thickness, or both is about 1-4 inches.

* * * * *